United States Patent
Heath

[19]

[11] Patent Number: 5,807,106
[45] Date of Patent: Sep. 15, 1998

[54] ENDODONTIC INSTRUMENT HAVING DEPTH CALIBRATIONS AND METHOD OF FABRICATING SAME

[76] Inventor: Derek E. Heath, 1917 Sherwood Dr., Johnson City, Tenn. 37604

[21] Appl. No.: 686,152

[22] Filed: Jul. 24, 1996

[51] Int. Cl.⁶ .................................................. A61C 3/02
[52] U.S. Cl. ................. 433/102; 408/226; 76/14
[58] Field of Search .................. 433/72, 75, 81, 433/102, 224; 408/202, 226, 241 S; 470/84; 76/14

[56] References Cited

U.S. PATENT DOCUMENTS

| | | | |
|---|---|---|---|
| 2,468,874 | 5/1949 | Hawkins | 408/226 |
| 2,886,291 | 5/1959 | Frisby | 175/40 |
| 3,562,913 | 2/1971 | Saffro | 433/75 |
| 3,842,632 | 10/1974 | Nelson . | |
| 4,028,810 | 6/1977 | Vice | 433/102 |
| 4,457,710 | 7/1984 | McSpadden | 433/81 |
| 4,527,449 | 7/1985 | Sydlowski et al. | 408/226 |
| 4,611,509 | 9/1986 | Matsutani . | |
| 4,871,312 | 10/1989 | Heath . | |
| 4,904,185 | 2/1990 | McSpadden | 433/102 |
| 5,106,298 | 4/1992 | Heath et al. . | |
| 5,118,297 | 6/1992 | Johnson | 433/224 |
| 5,464,362 | 11/1995 | Heath et al. . | |
| 5,527,205 | 6/1996 | Heath et al. . | |

FOREIGN PATENT DOCUMENTS

| | | | |
|---|---|---|---|
| 2 553 018 | 4/1985 | France . | |
| 2613212 | 10/1988 | France | 433/72 |
| 2022475 | 12/1979 | United Kingdom | 433/102 |

OTHER PUBLICATIONS

"Fenn Swaging Machines for Pointing, Reducing, or Shaping Wire, Tube or Rod Metal Forming Without Cutting Chips" brochure; The Fenn Manufacturing Company; 5 pages.

"Fenn Swaging Machines Service Manual" brochure; The Fenn Manufacturing Company; pp. 1–15.

*Primary Examiner*—Ralph A. Lewis
*Attorney, Agent, or Firm*—Bell Seltzer Intellectual Property Law Group of Alston & Bird LLP

[57] ABSTRACT

A method of fabricating an endodontic instrument having depth indicating calibrations formed between the handle and the fluted tapered end portion, and wherein the calibrations are formed by a cold rolling operation. The rolled calibrations do not form fracture points, they may be rapidly and inexpensively formed, and they have a smooth surface finish. Further, the rolled calibrations provide a sufficient physical indentation to be readily visible on x-ray photographs.

10 Claims, 3 Drawing Sheets

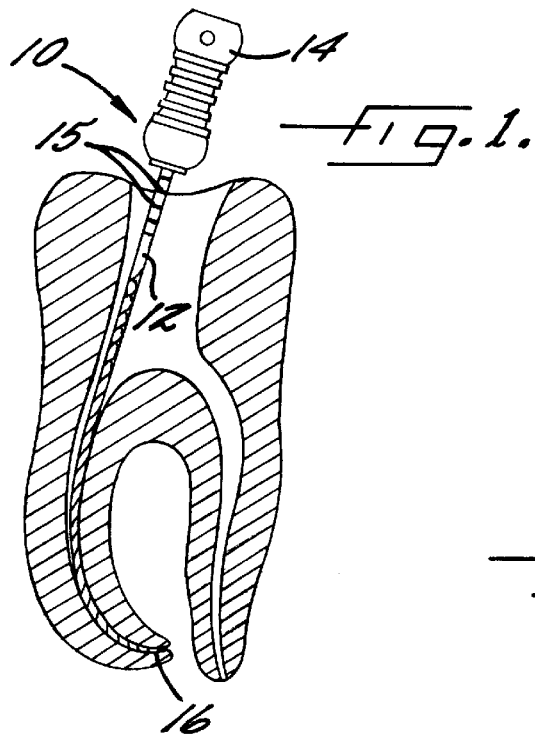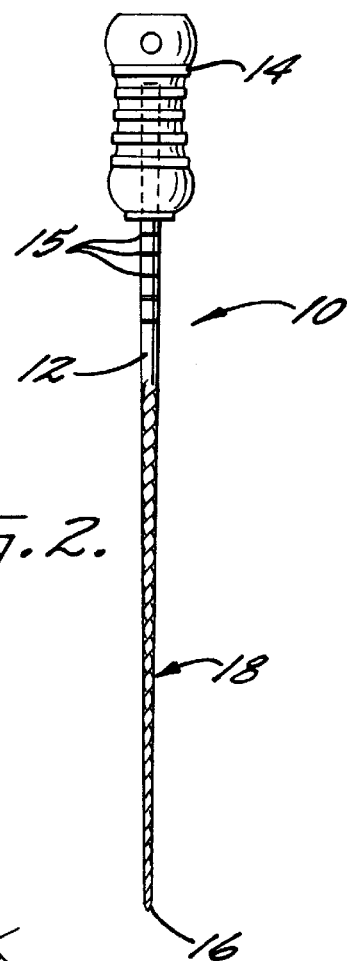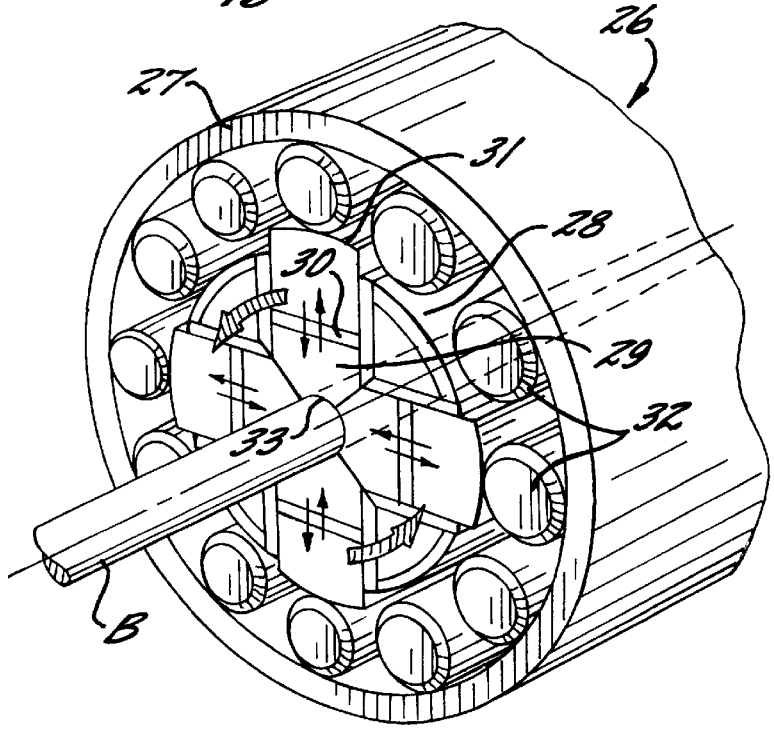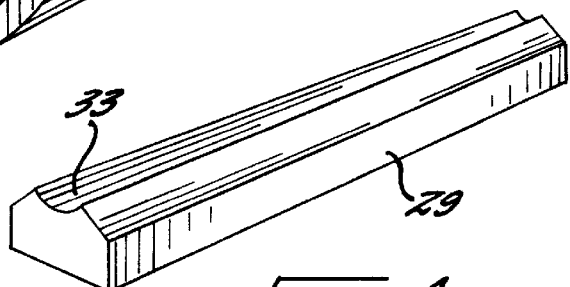

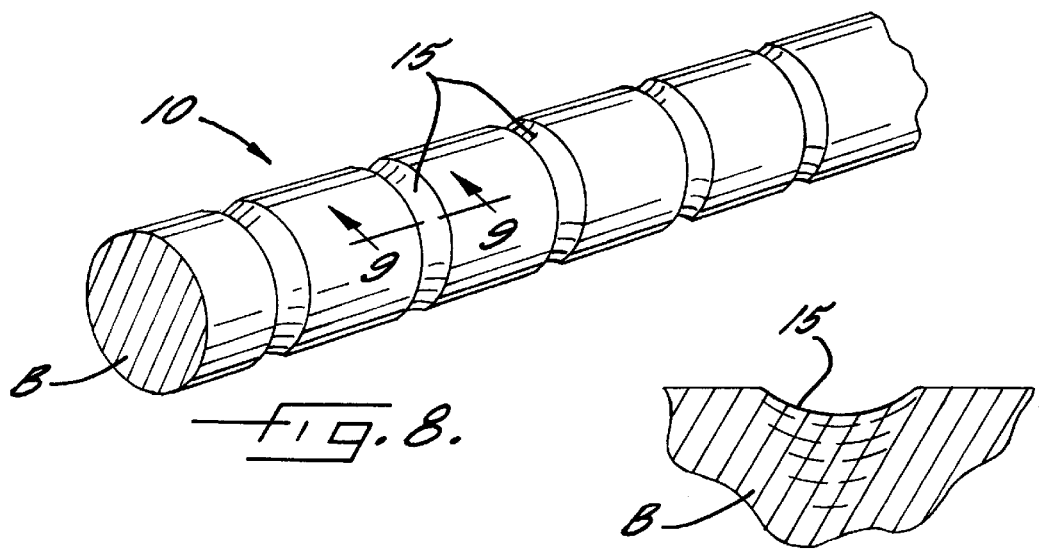
_Fig. 8._
_Fig. 9._
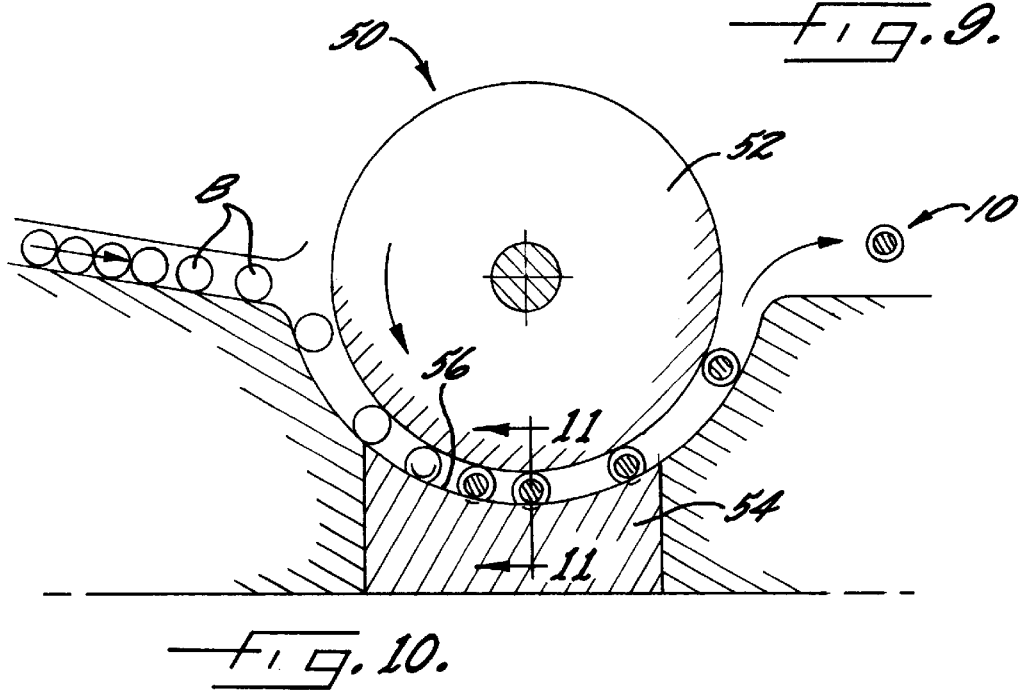
_Fig. 10._
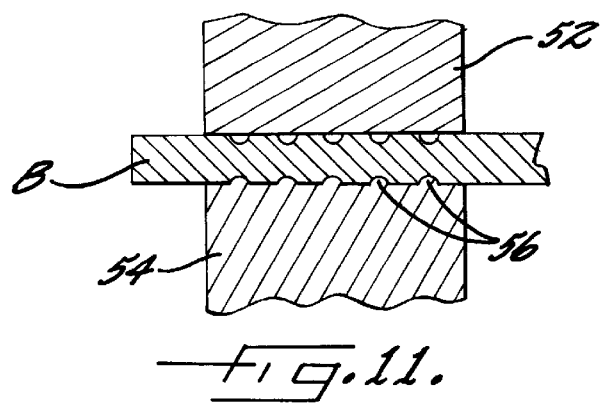
_Fig. 11._

ENDODONTIC INSTRUMENT HAVING DEPTH CALIBRATIONS AND METHOD OF FABRICATING SAME

BACKGROUND OF THE INVENTION

The present invention relates to an endodontic instrument adapted for use in performing root canal therapy on teeth, and which includes depth indicating calibrations.

Root canal therapy is a well-known procedure wherein the crown of a diseased tooth is opened so as to permit the canal to be cleaned and then filled. More particularly, a series of very delicate, flexible, finger-held instruments or files are used to clean out and shape the root canal, and each file is manually rotated and reciprocated in the canal by the dentist. Files of increasingly larger diameter are used in sequence, to achieve the desired cleaning and shaping. When the canal is thus prepared, it is solidly filled with a filling material, which typically comprises a waxy, rubbery compound known as gutta percha. In one procedure, the gutta percha is positioned on an instrument called a compactor, and the coated compactor is inserted into the prepared canal and rotated and reciprocated to compact the gutta percha therein. The dentist thereafter fills the tooth above the gutta percha with a protective cement, and lastly, a crown is fitted to the tooth.

Endodontic instruments of the described type were originally fabricated by permanently twisting a stainless steel rod of triangular or square cross section. The apices of the triangular or square cross section thus formed cutting edges which spiral along the length of the instrument. More recently, such instruments have been produced by a machining process, and wherein a cylindrical rod of stainless steel or nickel titanium alloy is cut into blanks of about two inches in length, and one end portion of each blank is tapered by machining the blank in a centerless grinding machine. Helical flutes are then machined on the tapered end portion, by moving the blank past a rotating grinding wheel and while the blank is slowly rotated to impart the desired helical configuration to the flutes. A cutting edge is thus formed along each side edge of each flute, and a helical land is preferably formed between the spiral flutes, as illustrated in U.S. Pat. No. 4,871,312 to Heath. A machining process as described above and which is particularly suitable for machining nickel titanium alloy is further described in U.S. Pat. Nos. 5,464,362 and 5,527,205 to Heath, et al., the disclosures of which are incorporated herein by reference.

Endodontic instruments of the described type also incorporate a plurality of depth indicating calibrations formed on the shank between the handle and the fluted end portion, by which the dentist is able to determine the depth to which the instrument has been inserted into the canal. Specifically, the instrument is inserted and an x-ray photograph is taken to determine whether the pilot end of instrument has reached the bottom or apex of the canal. When this has occurred, the dentist notes from the photograph the depth calibration aligned with the crown of the tooth, and this depth calibration is utilized during the continued extirpation process to insure that the instrument does not penetrate beyond the apex of the canal.

Since the calibrations must be visible in the x-ray photographs, they are presently formed by grinding a plurality of annular physical indentations or grooves about the periphery of the shaft. While such ground annular grooves serve well the requirement of being readily visible in x-ray photographs, they form potential fracture points which can break as the instrument is manipulated during the extirpation process. The breaking of the instrument while in the canal can raise serious problems, including the loss of the tooth.

It is accordingly an object of the present invention to provide an endodontic instrument which includes depth indicating calibrations which are visible in x-ray photographs, and which do not significantly weaken the instrument.

SUMMARY OF THE INVENTION

The above and other objects and advantages of the present invention are achieved by the provision of a novel manufacturing process which includes the steps of providing a cylindrical rod-like blank of metallic material and which has a diameter less than about 0.1 inches, and forming at least one helical flute on one end portion so as to extend along the length thereof, and such that the helical flute defines a cutting edge along each side edge thereof.

A plurality of axially spaced apart depth indicating calibrations are formed on the blank at a location spaced from the one end portion, with each of the calibrations being formed by cold rolling an annular groove about the blank. Further, a handle is mounted on the end of the blank so as to be engageable between the fingers of the user or by a machine driven handpiece.

The forming of the calibrations by the cold rolling operation, as opposed to the conventional grinding operation, has been found to effectively alleviate the breakage problem. More particularly, the cold rolling operation does not produce fracture points, it is faster and less expensive than grinding, and it produces a harder, more smooth surface finish in the groove. Further, the rolled grooves provide a sufficient physical indentation to be readily visible on x-ray photographs.

BRIEF DESCRIPTION OF THE DRAWINGS

Some of the objects and advantages of the present invention having been stated, others will appear as the description proceeds, when taken in conjunction with the accompanying drawings, in which:

FIG. 1 is a cross sections view of a tooth having two roots, with an endodontic instrument manufactured in accordance with the present invention being positioned in one of the roots;

FIG. 2 is a side elevation view of the instrument shown in FIG. 1;

FIG. 3 is a perspective view of a rotary swaging or cold forging machine suitable for forming a tapered end portion on the instrument;

FIG. 4 is a perspective view of one of the dies of the rotary swaging machine shown in FIG. 3;

FIG. 8 is a fragmentary perspective view of the portion of the instrument which includes the depth indicating calibrations which are formed in accordance with the present invention;

FIG. 9 is a fragmentary sectional view of one of the calibrations and taken along the line 9—9 in FIG. 8;

FIG. 10 is a schematic view of an apparatus for cold rolling the calibrations in the instruments; and FIG. 11 is a fragmentary sectional view taken along the line 11—11 of FIG. 10.

DETAILED DESCRIPTION OF THE PREFERRED EMBODIMENTS

Figure 6:
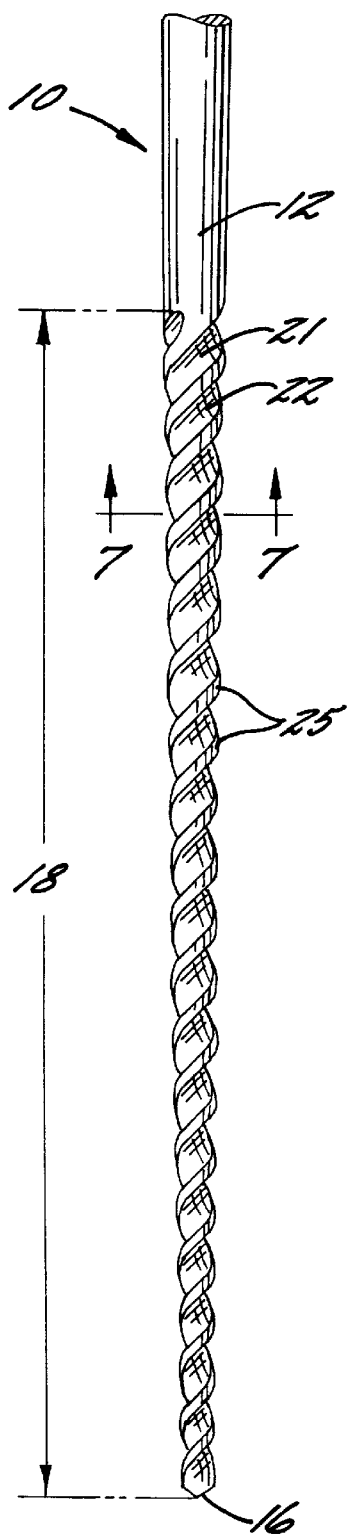
FIG. 6 is an enlarged side elevation view of the lower end portion of the instrument shown in FIGS. 1 and 2.
Figure 5:
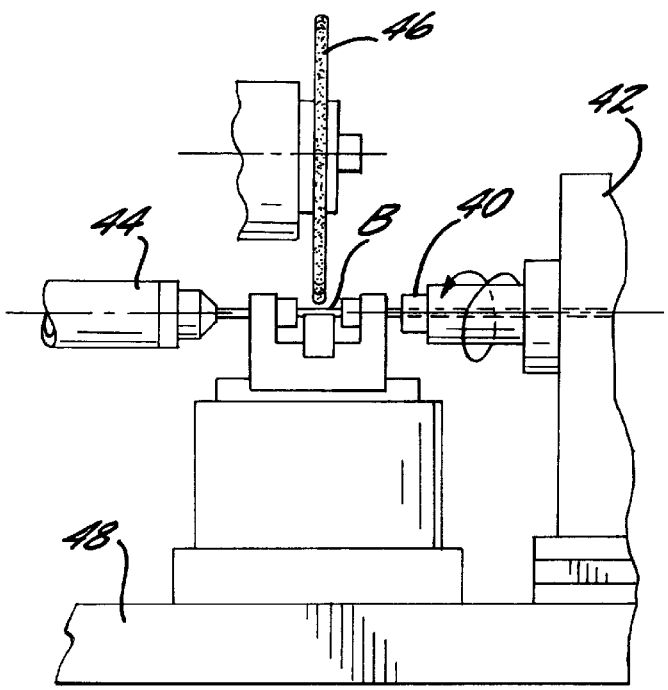
FIG. 5 is a schematic side elevation view of a machining apparatus suitable for forming the flutes in the instrument in accordance with the present invention.

Referring more particularly to FIGS. 1 and 2, an endodontic instrument 10 is illustrated which comprises a shank 12 which is preferably composed of stainless steel or a nickel titanium alloy as further described below. The shank 12 typically has a length of about 30 mm (1.2 inches), and it includes an outer or proximate end which mounts a conventional handle 14. The illustrated handle is of a configuration which is intended to be gripped between the fingers of the user, but the handle may alternatively be configured for engagement by a machine driven handpiece as known in the art.

The portion of the shank immediately below the handle is cylindrical and has a diameter of between about 0.5 and 1.6 mm (0.02 and 0.1 inches), and this shank portion includes depth indicating calibrations 15 as further described below. The shank further includes an opposite distal or pilot end 16, and a working length 18 is defined adjacent the pilot end 16. The working length is slightly tapered toward the pilot end 16 at an included angle of between about one half and eight degrees, preferably about one degree. The working length 18 may have a length of about 2 mm (0.08 inches) up to the full length of the shank 12, i.e. about 30 mm (1.2 inches). However, the working length 18 preferably has a length sufficient to extend substantially the full depth of a tooth root canal, which typically is about 16 mm (0.63 inches).

Figure 7:
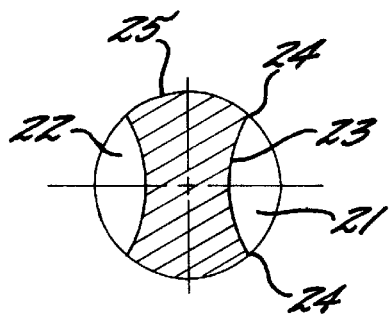
FIG. 7 is a transverse sectional view taken substantially along the line 7—7 of FIG. 6.

The peripheral surface of the working length 18 includes two continuous helical flutes 21, 22 formed therein. The flutes have an arcuate curvature as best seen in FIG. 7, and so as to define a curved concave bottom wall 23 and a cutting edge 24 along each side edge thereof. Also, the flutes have a pitch so as to define helical lands 25 on the outer periphery of the instrument and between axially adjacent flute segments. An instrument of this general construction is further described in U.S. Pat. No. 4,871,312 to Heath, and U.S. Pat. No. 5,106,298 to Health et al.

The method for producing the endodontic instrument as described above starts with a length of drawn wire of suitable metallic material, such as stainless steel or a nickel titanium alloy. A particularly suitable alloy comprises at least about 40% titanium and at least about 50% nickel and as further described in U.S. Pat. No. 5,464,362. The wire has a diameter of about 0.1 inches or less, and it is cut into blanks of about two inches in length by a conventional cutting operation. A conical taper is then formed on one end portion of the blank by machining the blank on a centerless grinder, or by cold forging the end portion of the blank, to define an included angle of between about ½ and 8°, as described above.

A rotary swaging machine suitable for cold forging the taper on the blanks is generally illustrated at 26 in FIGS. 3 and 4. In particular, the machine 26 includes an outer tubular frame 27, and a rotatable spindle 28 which is coaxially disposed within the tubular frame. The end of the spindle is slotted so as to accommodate four radially extending sets of a die 29, a shim 30, and a hammer 31. A roll cage, which includes a plurality of roller bearings 32, surrounds the spindle 28. The opposite end of the spindle is rotated by an electric motor (not shown), and as the spindle rotates, centrifugal force throws the dies 29, shims 30, and hammers 31 outward against the roll cage. Each time the hammers pass directly under a roller 32, they are driven inward, forcing the dies 29 to close and apply a forging stroke upon the blank B, which is placed coaxially inside the dies in the manner illustrated. As the hammers 31 pass out from under the rollers, the dies are again thrown open, ready for the next forging stroke. The forging strokes may be applied simultaneously by all of the hammers, or they may be applied alternately, depending upon the configuration of the rollers 32 in the roll cage. In the case of blanks formed of nickel titanium alloy, the spindle is preferably rotated at a speed sufficient to impart about 3500 forging strokes from each of the dies per minute, and it typically takes less than a second for the forging operation to be completed.

FIG. 4 illustrates in more detail the configuration of one of the forging dies 29 of the machine shown in FIG. 3. As illustrated, the operative upper surface of the die includes a U-shaped channel 33 along its length, with the channel being of decreasing depth toward the inner end of the die.

A rotary swaging machine 26 as illustrated and described above with reference to FIGS. 3 and 4 is conventional, and a suitable machine is manufactured by Penn Manufacturing of Newington, Conn., as model NF.

Upon completion of the cold forging operation, the tapered end portion of each blank is subjected to a machining operation which forms at least one, and preferably two or more helical flutes 21, 22 along the length thereof. More particularly, each blank B is mounted in a collet 40 at the forward end of an indexing block 42 of a conventional centerless grinding machine, with a work holding fixture 44 positioned to support the forward end of the blank adjacent the periphery of a rotating grinding wheel 46. The block 42 is then advanced so that the blank is axially moved past the rotating grinding wheel 46, while the blank is slowly rotated about its axis.

When the blank has advanced past the rotating wheel 46 a distance sufficient to form the first flute 21 along the desired working length on the instrument, the table 48 supporting the indexing block 42, and the fixture 44 is moved laterally, then axially rearwardly, and then laterally back to its original position. Concurrently, the blank is rotatably indexed about its axis. The angular extent of this blank indexing will depend upon the number of flutes desired on the finished instrument, and where three flutes are to be formed, the rod is indexed 120°. The blank is then again axially advanced while being slowly rotated, and so as to form the second flute 22. The table 48 is then again moved laterally and rearwardly in the manner described above, and the blank is rotatably indexed another 120°. The grinding process is then repeated to form the third flute of the instrument. Where the instrument has only two flutes as illustrated, the rod is indexed 180° between the two machining operations.

The outer periphery of the grinding wheel 46 is preferably curved in cross section, as opposed to being flat, and as a result the flutes have a curved concave bottom wall 23 when viewed in transverse cross section, and as seen in FIG. 7. Also, the grinding operation results in a sharp cutting edge 24 being formed along each side of the flute, and the helix angle imparted to the flutes is sufficient to form the helical land 25 between the axially adjacent flute segments.

A more detailed description of the machining process, and which is particularly suitable for machining nickel-titanium instruments, is disclosed in the above referenced U.S. Pat. No. 5,464,362.

At the conclusion of the above operations, the calibrated depth markings 15 are formed on each blank, and the handle 14 is attached to the end of the blank which is opposite the working length. The calibrations 15 are formed by a cold rolling operation as schematically illustrated in FIGS. 10 and 11. A modified conventional thread rolling machine 50 may be employed for this operation, and which comprises a rotary cylinder 52 and an arcuate die plate 54 which is fixed so as to underlie a portion of the lower periphery of the cylinder 52. The die plate 54 includes a number of ridges or projections 56 which are perpendicular to the axis of the cylinder, and which form the calibrations 15 as the blanks are fed through the arcuate slot between the cylinder 52 and the die 54 by the rotation of the cylinder 52. The operation is extremely fast, and results in the calibrations being cold rolled in the form of annular grooves of arcuate configuration as seen in FIG. 9. These cold rolled calibrations do not appreciably weaken the instrument, and the formation of fracture points is thereby avoided.

In the drawings and the specification, there has been set forth preferred embodiments of the invention and, although specific terms are employed, the terms are used in a generic and descriptive sense only and not for the purpose of limitation, the scope of the invention being set forth in the following claims.

That which is claimed is:

1. A method of fabricating an endodontic instrument suitable for extirpating and shaping a root canal during root canal therapy, and comprising the steps of providing a cylindrical rod-like blank of metallic material and which has a diameter less than about 0.1 inches, machining at least one helical flute in the blank and so that the one flute extends along one end portion of the blank, and such that the one helical flute defines a cutting edge along each side edge thereof, and forming a plurality of axially spaced apart depth indicating calibrations on the blank at a location spaced from said one end portion, and including forming each of the calibrations by cold rolling an annular groove about the blank.

2. The method as defined in claim 1 wherein the step of machining at least one helical flute includes machining the one flute so as to have a curved concave bottom wall when viewed in transverse cross section, and wherein a helical land is positioned between axially adjacent flute segments.

3. The method as defined in claim 2 wherein the blank is composed of an alloy comprising at least about 40% titanium and at least about 50% nickel.

4. The method as defined in claim 3 wherein the blank has a length of about two inches.

5. The method as defined in claim 3 comprising the further step of forming a conical taper on the one end portion of the blank and prior to the step of forming at least one helical flute, with the taper defining an included angle of between about ½ and 8°.

6. An endodontic instrument suitable for extirpating and shaping a root canal during root canal therapy and which is produced in accordance with the method defined in claim 1.

7. A method of fabricating an endodontic instrument suitable for extirpating and shaping a root canal during root canal therapy, and comprising the steps of providing a cylindrical rod-like blank which is composed of an alloy comprising at least about 40% titanium and at least about 50% nickel, and which has a diameter less than about 0.1 inches, forming a conical taper on one end portion of the blank, with the taper having a length of about 0.08 inches and defining an included angle of between about ½ and 8°, and machining at least one helical flute so as to extend along the length of the tapered end portion of the blank, and such that the helical flute defines a cutting edge along each side edge thereof, said machining step including forming the one flute so as to have a curved concave bottom wall when viewed in transverse cross section, and wherein a helical land is positioned between axially adjacent flute segments, and forming a plurality of axially spaced apart depth indicating calibrations on the blank at a location spaced from said one end portion, and including forming each of the calibrations by cold rolling an annular groove about the blank.

8. The method as defined in claim 7 comprising the further step of applying a handle to the end of the blank opposite the one end portion, so that the plurality of axially spaced apart depth indicating calibrations are positioned between the handle and the one end portion of the blank, and with the handle being configured to be engageable between the fingers of the user or by a machine driven handpiece.

9. The method as defined in claim 8 wherein the blank has a length of about two inches.

10. An endodontic instrument suitable for extirpating and shaping a root canal during root canal therapy and which is produced in accordance with the method defined in claim 8.

* * * * *